United States Patent [19]

Danby et al.

[11] Patent Number: 4,674,722
[45] Date of Patent: Jun. 23, 1987

[54] MEDICAL ACCESSORY POLE CLAMP

[75] Inventors: Hal C. Danby, Sudbury, England; Carl Ritson, San Jose, Calif.

[73] Assignee: Critikon, Inc., Tampa, Fla.

[21] Appl. No.: 799,234

[22] Filed: Nov. 18, 1985

[51] Int. Cl.4 .............................................. E04G 3/00
[52] U.S. Cl. ........................... 248/231.3; 248/231.5;
 248/124; 24/569; 24/134 R; 24/134 KB;
 403/350; 403/374
[58] Field of Search ............... 248/231.3, 230, 231.5,
 248/124; 24/569, 534, 535, 543, 134 R, 134 P,
 134 WL, 134 KB, 33 J; 604/34, 250; 251/9;
 403/350, 374, 409.1

[56] References Cited

U.S. PATENT DOCUMENTS

| 419,379 | 1/1890 | Talbot | 248/231.3 |
|---|---|---|---|
| 1,382,046 | 6/1921 | Zimmerman, Jr. | 24/134 R |
| 1,410,162 | 3/1922 | Cadwell | 24/134 R |
| 2,584,955 | 2/1952 | Williams | 248/231.3 |
| 3,251,107 | 5/1966 | Scott | 24/134 R |
| 3,265,032 | 8/1966 | Hume | 24/134 R |
| 3,730,129 | 5/1973 | Helms | 24/134 R |
| 3,765,061 | 10/1973 | Nash | 24/134 KB |
| 3,901,231 | 8/1975 | Olson | 128/DIG. 13 |
| 4,217,847 | 8/1980 | McCloud | 24/134 KB |
| 4,383,252 | 5/1983 | Purcell et al. | 248/124 |

Primary Examiner—Richard J. Scanlan, Jr.
Assistant Examiner—Douglas W. Hanson
Attorney, Agent, or Firm—William B. Walker

[57] ABSTRACT

A mounting clamp particularly suited for mounting medical accessories on support poles comprises a stationary clamping surface which can be attached to an accessory housing. A cam is pivotly mounted on a trunnion connected to the stationary clamping surface has a spiral clamping surface, the stationary clamping surface and spiral clamping surface being positioned to constitute a clamping means when the clamp is in a clamping position. A spring means having one end connected to the trunnion and the other end connected to the cam is provided for biasing the cam to the clamping position. A lever pivotly mounted on the trunnion has a projection which engages the cam and causing it to pivot with the lever when the lever is pivoted to a clamp releasing position. The cam preferably has two spiral surfaces, one generated by a line parallel to the axis of rotation of the cam and the second cam surface by a line forming an angle with the axis of rotation of the cam. Two stationary surfaces preferably oppose the two cam surfaces, whereby the clamp bears on a total of four surfaces of a support pole when fully secured.

19 Claims, 13 Drawing Figures

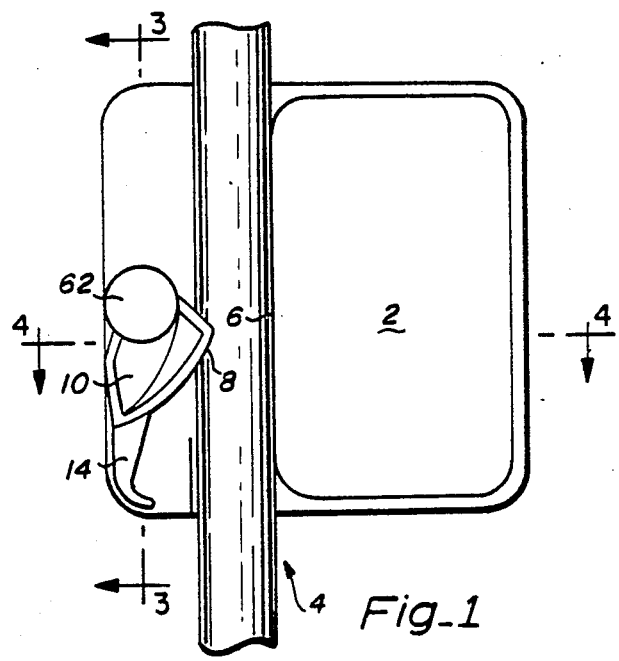
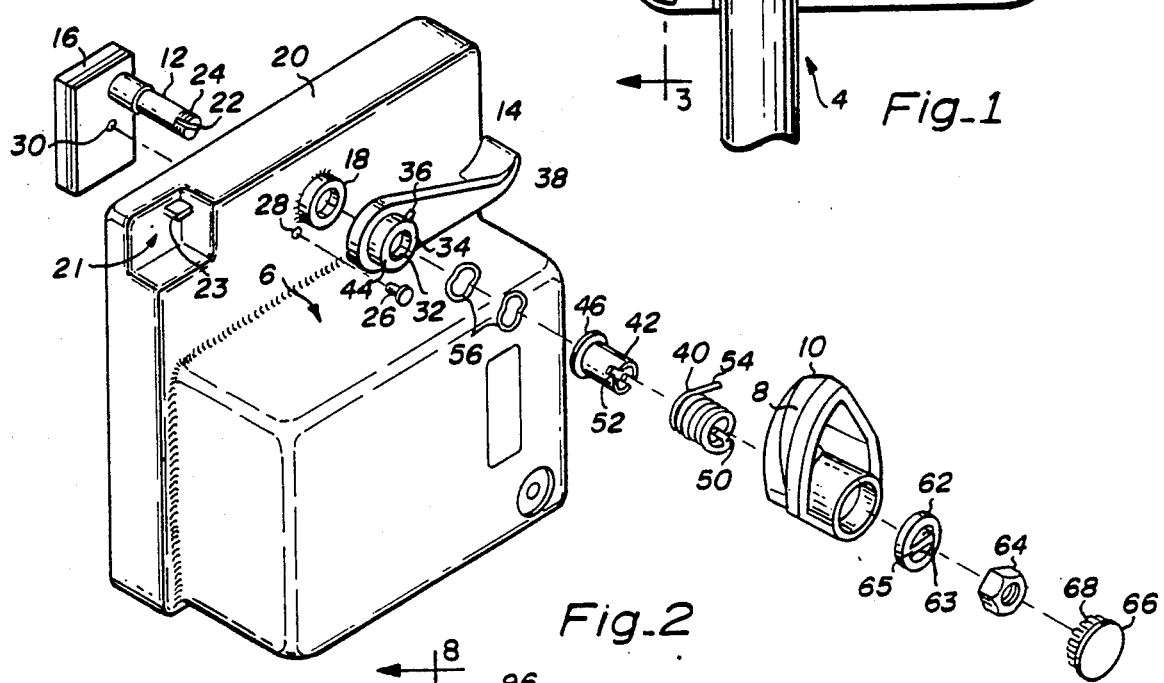
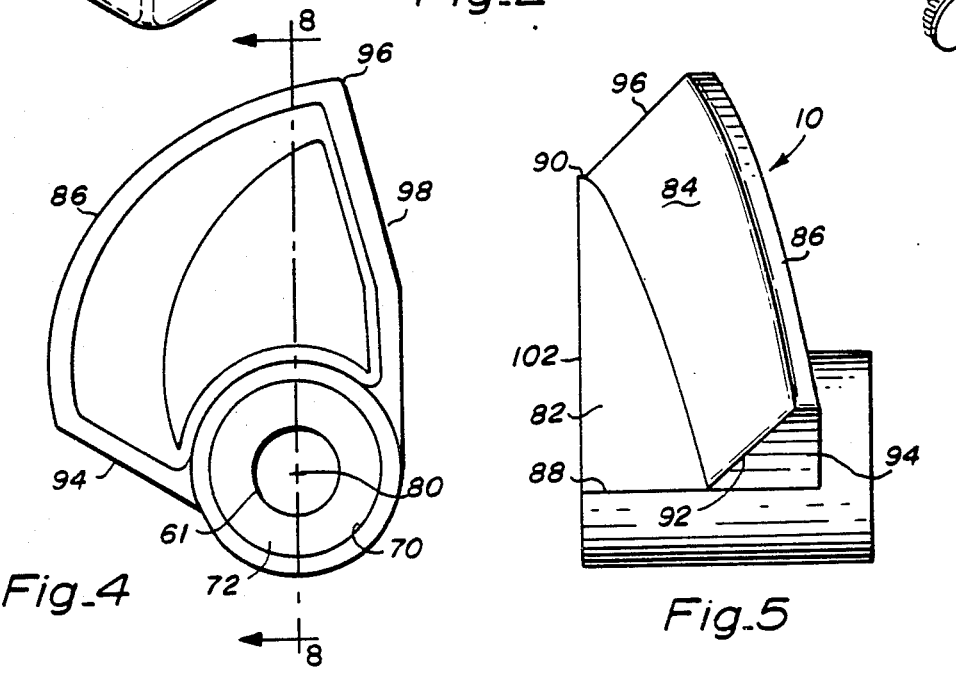

MEDICAL ACCESSORY POLE CLAMP

FIELD OF THE INVENTION

This invention relates to an apparatus for mounting a housing on an elongated supporting member. In particular, this invention is directed to an apparatus for releasably mounting a device such as a parenteral solution flow controller on a support pole in a medical environment.

BACKGROUND OF THE INVENTION

Medical practice has increasingly relied upon control systems, monitors and other automated accessory devices in providing patient care in the hospital environment and clinical environment. In minimizing equipment costs, many of the devices are portable and are moved from site to site in the hospital and clinic as needed. Mounting elements such as vertical poles are often provided as permanent structures where portable devices will be needed. This invention is an improved clamping system which is suitable for releasably mounting medical accessories on such elongated mounting members.

DESCRIPTION OF THE PRIOR ART

Adjustable mounting clamps such as the rod and manual knob descibed in U.S. Pat. No. 4,314,567 are commonly used for mounting devices on vertical poles, but they lack the convenience of a lever system.

Levered cam clamping systems have been widely used in the non-hospital environment. In general, these constructions involve an integral cam and lever arm for pivoting the cam about an axis. As the cam is rotated, the leverage of the arm is multiplied by the cam to increase the clamping pressure and increase the stability of the clamping action. In these systems, the increased pressure is absorbed by flexure of the components of the clamp and/or the element being clamped. U.S. Pat. No. 2,219,969 describes a holder for agricultural implements including an integral lever and cam. A tension spring mounted to the lever and frame pulls the lever in a direction which forces the cam into a clamping position, preventing unintentional release of the clamp. U.S. Pat. No. 3,016,225 showing a lever arm with an integral cam surface clamp for mounting concrete forms on a stake. U.S. Pat. No. 3,793,682 discloses a rope clamp comprising a cam with flat locking surfaces and an integral lever. The lever is rotated to lock a fixture to a wire cable. U.S. Pat. No. 4,123,026 describes a camera attachment for releasably holding a camera accessory such as a flash lamp. The device includes a lever and integral cam which increases or releases tension on a support band in which a portion of the accessory is positioned to clamp the accessory in position or release it. U.S. Pat. No. 4,487,523 discloses an accessory clamp for an abductor bar. A manually adjustable knob and screw element is used to adjust the distance between clamping elements of an accessory mounting bracket. An integral cam and lever pivotly mounted on one element of the abductor bar clamp acts on the second clamping element to pivot the respective clamping elements relative to each other into an engaging position about an abductor bar. The cam surface of the lever engages an adjustable, spring biased rod mounted in the second clamping element.

U.S. Pat. No. 3,251,107 is directed to a vacuum cleaner cord locking device which includes an integral cam and lever locking system. A torsion spring engaging the cam and housing urges the cam into a clamping position, maintaining cam pressure on the cord and preventing its release until the lever is lifted to release the lock.

U.S. Pat. No. 3,852,943 discloses a safety clamp comprising a lever with an integral cam surface mounted to a housing wall by means of a trunnion pin. A torsion spring mounted on the pin engages the housing and pin. It maintains the angle of the cam in an engaging position and biases the cam surface lightly against a support rope. If light engagement is maintained, movement of the clamp housing in an undesired direction on the rope pulls the cam surface tightly into the rope, locking the housing and the rope, and preventing further movement of the housing relative to the rope.

SUMMARY OF THE INVENTION

This invention is directed to an improved clamping device comprising a first clamping member, a cam, a lever and a spring. The cam is mounted for rotation from a non-engaging position to a clamping position and is positioned with respect to the first clamping member to clamp an elongated member between the cam and first clamping member when the cam is in the clamping position. The lever mounted for pivotal rotation includes a means for engaging the cam when the lever is pivoted in a releasing direction and for rotating the cam to a non-engaging position. A spring means connected to the cam and biasing the cam into a clamping position is placed under increased tension or compression when the cam is rotated by pivotal movement of the lever to a non-engaging position. When the lever is released, the tension or compression bias of the spring returns the cam to a clamping position. In the preferred embodiment, the cam, lever and spring are mounted about a common trunnion, and the spring is a torsion spring having one end secured to the trunnion and the other end engaging the cam.

BRIEF SUMMARY OF THE DRAWINGS

FIG. 1 is a view of the combination of a device housing, clamping assembly and mounting pole of one embodiment of this invention.

FIG. 2 is an exploded view of the device housing and clamping assembly elements of the embodiment shown in FIG. 1.

FIG. 4 is front view of the cam element of the embodiment of this invention shown in FIGS. 1-3.

FIG. 5 is a left side view of the view of the cam element shown in FIG. 5.

DETAIL DESCRIPTION OF THE INVENTION

Figure 3:
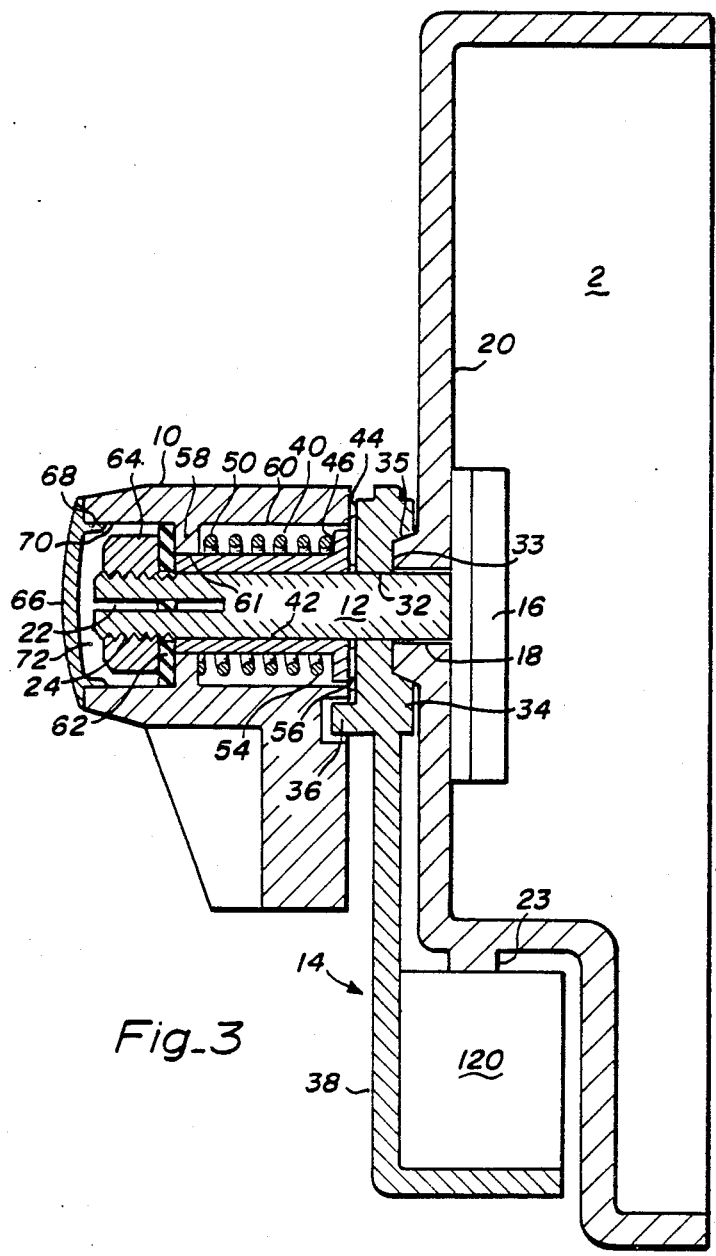
FIG. 3 is a cross-sectional view of the clamp assembly elements taken along the line 3—3 in FIG. 1.

A frontal view of the device of this invention in a clamping position is shown in FIG. 1. The housing 2 encloses the device to be releasably mounted on the elongated support member or pole 4. The clamping surface 6 of the housing 2 faces and is opposed to the cam engaging surface 8 of the cam 10. The cam is pivotally mounted on the trunnion or rod 12 (shown in FIGS. 2 and 3). In the position illustrated in FIG. 1, the cam is pivoted to the maximum clockwise or clamping position. The lever 14, described in greater detail in conjunction with FIGS. 2 and 3 below, is pivotally mounted axially concentric with the commonly mounted cam 10. Movement of the lever 14 in a counterclockwise direction engages the cam 10 and pivots it in a counterclockwise direction to a releasing position.

In the engaged position of the cam 10, the pole 4 is securely held between the cam engaging surface 8 and the housing engaging surface 6, and the housing 2 is thus securely mounted on the pole 4.

FIG. 2 is an exploded view of the device housing and clamping assembly elements, and FIG. 3 is a cross-sectional view of the clamp assembly elements taken along the line 3—3 in FIG. 1. The trunnion 12 is mounted on the trunnion plate 16, and when assembled with the housing 2, passes through the hole 18 in the integral housing flange 20 and is supported thereby. The unsecured end of the trunnion 12 has a spring engaging slot 22 and threads 24. The trunnion plate mounting screw 26 passes through a hole 28 in the flange 20 and engages the threaded hole 30 of the trunnion plate 16, securing the trunnion plate 16 to the housing flange 20. The housing flange 20 has a lever recess 21 with an integral lever stop 23.

The lever 14 is pivotally mounted on the trunnion 12 passing through its bearing hole 32 and includes a boss 34 with cam engaging projection 36 and handle portion 38. The reverse side of the boss 34 has a frustoconical recess 33 which receives and frictionally engages the tapered boss 35 of the housing flange 20.

The torsion spring 40 is mounted in the cam 10. The surface of the sleeve bearing 42 facing the outward opposing surface 44 of the lever boss 34 is an outwardly extending flange portion 46. The end 50 of the torsion spring 40 extends across the axial center of the spring for engaging the slot 52 in the end of the sleeve bearing 42 and the slot 22 of the trunnion. The other end 54 of the spring extends tangentially outward for engaging an inner surface of the cam 10. Two wavy washers 56 are positioned between the lever flange surface 44 and the sleeve bearing flange 46 to facilitate movement therebetween.

The cam 10 has a cylindrical, axial recess 60 which receives the spring 40, and an integral hub 58 having an opening 61 through which the sleeve bearing 42 extends in supporting engagement. The slotted and threaded end of the trunnion 12 and the slotted end 52 of the sleeve bearing 42 extend through and beyond the axial opening 61. A washer 62 has two, opposed semicircular openings 63 for receiving and engaging the slotted end of the trunnion 12, the transverse bar separating the openings 63 engaging the slot 22 in the end of the trunnion. The nut 64 engages the trunnion threads 24 and secures the cam 10, sleeve bearing 42, washers 56 and lever 14 on the trunnion 12. Tightening nut 64 increases pressure between the flange 46 of the sleeve bearing, and the lever boss surface 44, and the wavy washers 56 therebetween. This pressure is transmitted to the sliding surfaces of the lever recess 32 and the housing boss 35. Nut 64 can be adjusted to set the moving friction of the system to prevent snap-back of the lever if it is accidentally released.

Conventional cap 66 can be used to cover the nut 64, the mounting tines 68 thereof pressing outward in frictional engagement with the opposed inner surface 70 of the cam recess 72.

FIGS. 4-8 are front, back, side and cross-sectional views of the cam 10 in the embodiment of the invention described above in conjunction with FIGS. 1-3.

Referring to FIGS. 4 and 5, the cam 10 is supported by the trunnion 12 (FIGS. 2 and 3) which passes through the hole 61. The cam 10 pivots about its axis 80, rotating in a clockwise direction to release the clamping action and spring biased to rotate in the counterclockwise direction when the lever 14 (FIG. 1) is released. FIG. 5 is a left side view of the cam 10 shown in FIG. 4 and shows the cam surfaces 82 and 84. Edge 86 is the limit of the cam surface 84.

Figure 6:
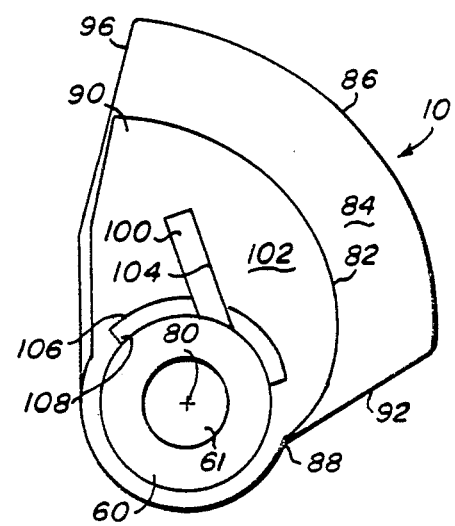
FIG. 6 is a back side view of the cam element shown in frontal view in FIG. 4.
Figure 7:
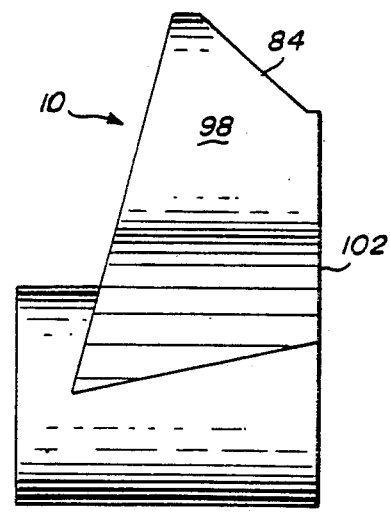
FIG. 7 is a left side view of the cam element shown in back view in FIG. 6 and right side view of the cam element as shown in the frontal view in FIG. 4.

FIGS. 6 and 7 show the back and right side view of the cam 10 as shown in FIG. 4.

Referring to FIGS. 5 and 6, cam surface 82 is a spiral surface generated by a line having an axis parallel to the cam axis 80. The distance between the line at any point and the axis increases as the line moves in a counterclockwise track (FIG. 6) from its initial position 88 to the terminal position 90. The spiral surface thus generated advances the cam surface radially outward as the cam rotates in the counterclockwise direction from the perspective of FIG. 6.

Cam surface 84 is generated by a line forming an angle of approximately from about 25 to 65, preferably from 35 to 55 and optimally about 45° with the axis 80. The surface 84 begins at the initial edge 92 (minimal distance from the axis 80) which is the intersection of a plane 94 and the cam surface 84, the plane 94 being approximately parallel to (within 15° of the axis 80) but not passing through the cam axis 80. The surface 84 ends at the terminal edge 96 (maximum distance from the axis 80) which is the intersection of a plane 98 and the cam surface 84, the plane 98 also being approximately parallel to but not passing through the cam axis 80. As the cam pivots in the counterclockwise direction (from the perspective of FIG. 6), the cam surface 84 advances radially outward from the cam axis 80.

Figure 8:
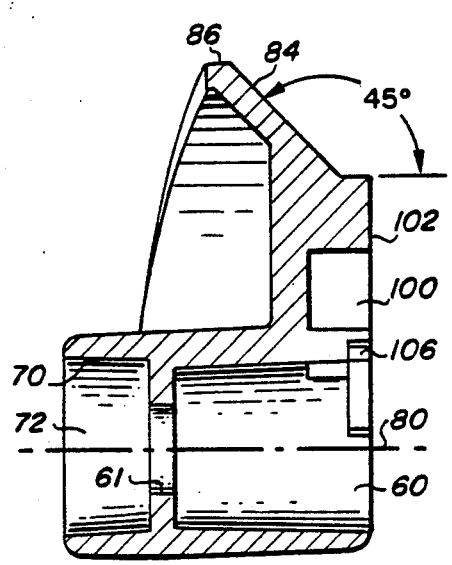
FIG. 8 is a cross-sectional view of the cam element taken along the line 8—8 in FIG. 4.

FIG. 8 is a cross-sectional view of the cam 10 taken along the line 8—8 in FIG. 4. The cam surface surface 82 can be seen to be approximately parallel to the axis 80 and the cam surface can be seen to form an angle of 45° with the axis 80.

Referring to FIGS. 6 and 8, the spring receptor slot 100 is formed in the rear face 102 of the cam 10. When the torsion spring 40 (FIG. 2) is inserted into the spring receptor 60, the extended end 54 of the spring is received by the recess 100, securing the extended spring end 54 to the cam for movement therewith. The spring is placed under torsional stress the extended end 54 (and cam 10), being rotated one full turn in the counterclockwise direction (from the perspective of FIG. 6) during assembly. The spring extension 54 bears against the recess surface 104, urging the cam in the clockwise direction from the perspective of FIG. 6. In this manner, the cam surfaces 82 and 84 are spring biased to advance in the direction toward the opposed clamping surfaces of the housing 2. The rear face 102 of the cam 10 also has an arcuate lever engaging recess 106 for receiving the projection 36 of the lever 14. When the lever 14 is rotated in a counterclockwise direction from the perspective of FIG. 6 (clockwise direction in the perspective of FIG. 1), the lever projection 36 engages the lever recess surface 108 and turns cam 10 in the same direction, against the bias of the spring 40. The cam surfaces 82 and 84 are thus retreated from the opposing clamping surfaces of the housing, releasing the clamp.

When the lever 14 is released, the spring 40 biases the cam 10 to pivot in the clockwise direction from the perspective of FIG. 6, advancing the cam surfaces 82 and 84 toward the object being clamped. The surface 106, continuing in engagement with the lever projection 36, rotates the lever toward the resting position shown in FIG. 1. If a support member such as a mounting pole is positioned between the cam 10 and the housing, the cam rotates to a resting position leaving the lever 14 extended from the housing. The lever can be further manually depressed, the lever projection 34 moving along the arcuate recess 106 until the lever handle engages the housing stop 23 in the lever handle recess 21 (see FIG. 2).

When no object is present between the cam surfaces 82 and 84 and the housing, the constant bias of the spring 40 continues to turn the cam in a clockwise direction from the perspective of FIG. 6. The lever rotation is limited in this direction by the housing stop 23, and engagement of the recess surface 108 with the lever projection 36 thus limits rotation of the cam 10 in the clockwise direction.

Figure 9:
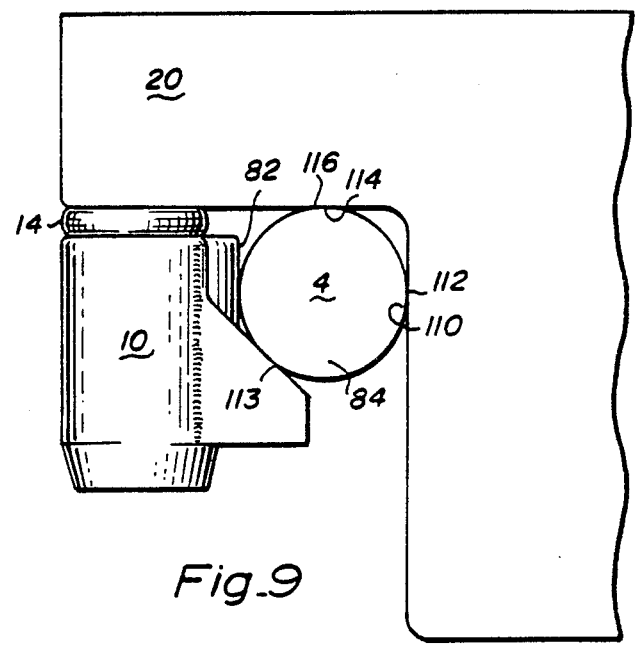
FIG. 9 is a partial top view of the combination of the device housing, clamping assembly and mounting pole shown in FIG. 1.

Referring to FIG. 9, a partial top view of the combination of the housing, clamping assembly and mounting pole of FIG. 1 is shown. The relative position of the cam surfaces, housing and object being clamped are shown.

When the cam as shown in FIG. 6 rotates, under the bias of the spring 40, in the clockwise direction, the cam surfaces 82 and 84 advance and approach opposed surfaces 112 and 114 of housing. The combination of the clamping surfaces 82 and 84 and the opposed surfaces 112 and 114 thus constitute the contacting surfaces of the support clamp of this invention. As cam surface 82 advances, it presses the pole 4 toward the opposing housing surface 112 until the pole surface 110 engages the housing surface 112. As cam surface 84 advances, contacting pole surface 113, the pole is advanced toward the other housing clamping surface 114 until the pole surface 116 engages the housing surface 114. The combined vectors of the cam surface pressures thus clamps the pole against the corner formed by the surfaces 110 and 114, providing a secure engagement.

The contact clamping surfaces 110 and 114 of the housing 20 preferably have a high friction coating or a high friction layer on the surface thereof to increase static friction when the clamp engages a support pole. Alternatively, thicker, resilient high friction pads can be secured to the clamping surfaces 110 and 114. Such pads (not shown) would yield under the pressure of a mounting pole under clamping pressure. Such yielding would increase the surface area of high friction contact with the pole, further increasing the static friction between the clamping surfaces and the pole surface. Each of these embodiments are intended to be included in this invention.

Figure 10:
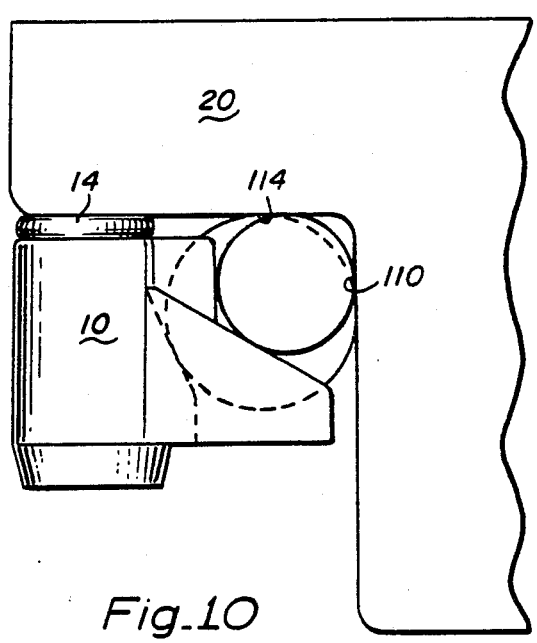
FIG. 10 is a partial top view of the combination of the device housing, clamping assembly and mounting pole shown in FIG. 9, showing the relative positions of the cam element when engaging small and large diameter mounting poles.

FIG. 10 is a partial top view of the combination of the device housing, clamping assembly and mounting pole shown in FIG. 9, showing cam positions for both small and large diameter mounting poles. The double cam 10 is self-adjusting to the diameter of the poles, biased by the torsion spring 40 to rotate until the cam surfaces press firmly against the pole surface. The position of the cam 10 for the small diameter pole 5 is shown in solid lines, and the position of the cam 10 for the large diameter pole 7 is shown in broken lines.

The device clamping surfaces have been shown as two right angle surfaces in the drawings, one parallel to the axis of rotation of the cam and the other perpendicular to the axis of rotation of the cam. This configuration is presented as representative of an optimum configuration. Any other relative angles which would allow efficient self-adjusting action between the clamping surfaces of the cam and the housing can be used and are intended to be included within the scope of this invention.

Figure 11:
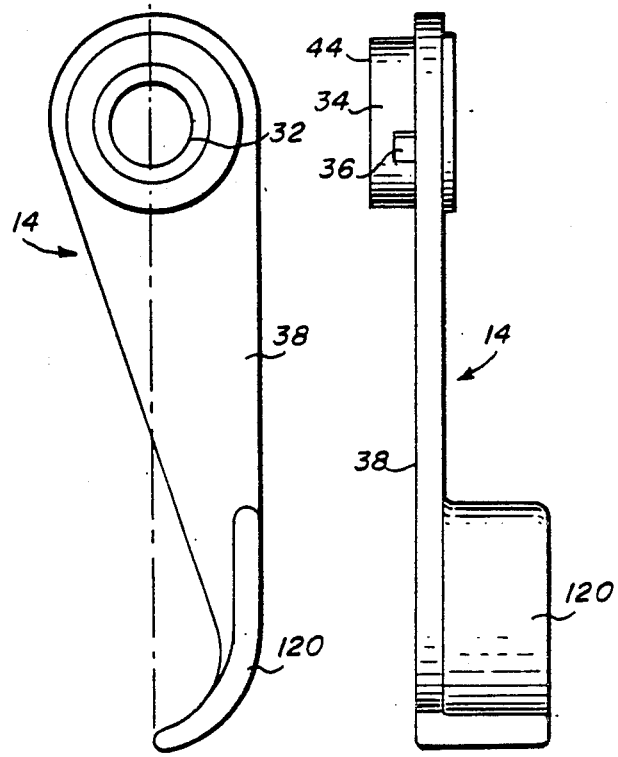
FIG. 11 is a front view of the lever in the embodiment of the invention shown in FIGS. 1—4.
Figure 12:
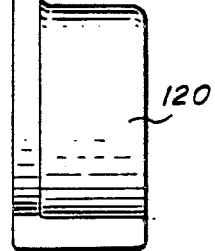
FIG. 12 is a right side view of the view of the lever shown in FIG. 11.

FIGS. 11 and 12 show details of the construction of the lever 14. The lever handle 38 is integral with the boss 34 and the cam engaging projection 36. The end of the handle 38 has a wing 120 which extends from the handle toward the housing. This wing increases the surface for manual contact in operating the lever and abuts the housing projection 23 (FIGS. 2 and 3) to limit movement of the lever and cam when not engaging a support member.

Figure 13:
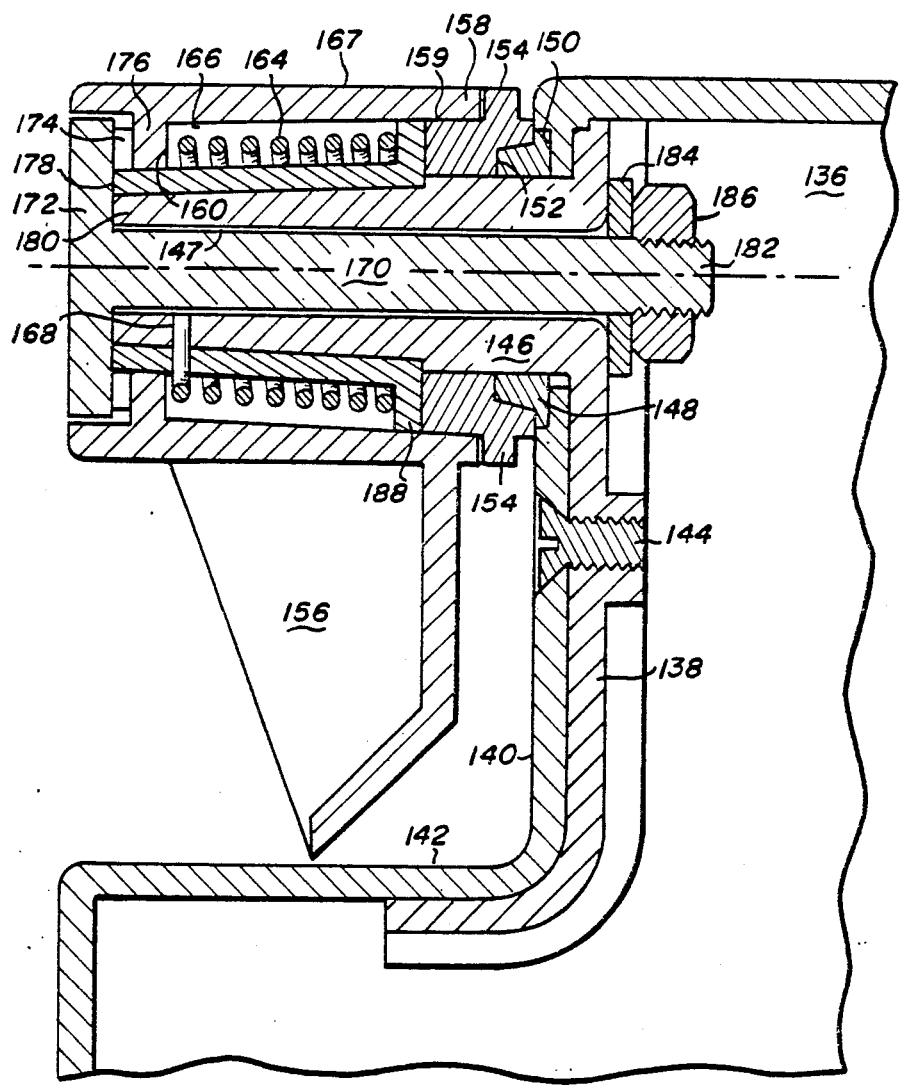
FIG. 13 is a cross-sectional top view of the combination of cam, lever and housing of another embodiment of this invention.

FIG. 13 is a cross-sectional top view of the combination of cam, lever and housing of another embodiment of this invention. A plate 138 extends behind the clamping surfaces 140 and 142 of the housing 136, mounted to the housing by screw 144, for example. The plate 138 thus reinforces the clamping areas 140 and 142 of the housing 136. Integral with the plate 138 is a trunnion 146, a tapered elongated rod-shaped extension having a hole 147 through its central axis. A washer 148 is positioned in the circular housing receptor 150 between the housing and the receptor 152 of the lever hub 154. The lever handle extends downward from the hub 154 and is not shown in this view. The cam 156 has end 158 mounted on the cylindrical boss 159 of the lever hub 154 and the other end 160 mounted on the external surface of the tapered sleeve bearing 162. The torsion spring 164 is positioned in the cam recess 166 between the cam drum 167 and the sleeve bearing 162. The end 168 of the spring 164 is secured against rotation, pinned against a flat side surface (not shown) of the bolt 170 which extends through the hole 147 of the trunnion 146. The bolt head 172 bears against a washer 174 between the bolt head and the flange 176 of the cam 156, against the end 178 of the sleeve bearing 162, and the end 180 of the trunnion 146. The threaded end 182 of the bolt is secured against the inner wall of the plate 138 by washer 184 and nut 186. Tightening the nut 186 forces the flange 188 of the sleeve bearing 162 against the lever hub 159, increasing the compression on the washer 148 and friction between the washer 148, the lever hub 154 and the housing receptor 150. The friction between the lever hub 159 and the washer 148 can thus be set, in a manner similar to that described above with respect to the embodiment of this invention described in FIGS. 1–12, to prevent snap-back of the lever and cam 156 if the lever is accidentally released when the cam is being held by the lever in a fully open position as when the housing is being mounted on a support pole.

The pole clamp of this invention permits easy adjustment for mounting, and the spring-biased, two cam surface configuration of the cam provides four friction bearing, contact points on a cylindrical mounting element such as a pole. Two cam surfaces bear on the pole, forcing it against two opposed surfaces of the housing, a total of four friction bearing points. This provides a more secure engagement. Furthermore, the mounting procedure is facilitated by the construction of the cam and separate lever, with the adjustments available to set the friction between the lever and cam assembly and the housing.

We claim:

1. A combination of a parenteral solution delivery system and an acessory clamping device comprising a system housing having a first stationary clamping surface attached thereto, a cam pivotally mounted on a trunnion connected to said system housing and havind a moveable clamping surface, the stationary clamping surface and moveable clamping surface being positioned to constitute a clamping means when the clamp is in a clamping position, a spring means having one end connected to the trunion and the other end connected to the cam for biasing the cam to the clamping position, a lever means pivotally mounted on the trunion for pivotal movement in a clamp releasing direction and in an opposite clamping direction, the lever means being mounted for pivotal movement independent of the pivotal movement of the cam, the lever means being connected to a cam engaging means for engaging the cam and causing it to pivot with the lever when the lever is pivoted in a clamp releasing direction and for releasing the cam and permitting it to return to the clamping position as the lever is pivoted in the clamping direction.

2. An acessory clamping device comprising a stationary clamping surface, a cam pivotally mounted on a trunnion connected to the stationary clamping surface and having a moveable clamping surface, the stationary clamping surface and moveable clamping surface being positioned to constitute a clamping means when the clamp is in a clamping position, a spring means having one end connected to the trunnion and the other end connected to the cam for biasing the cam to the clamping position, a lever means pivotally mounted on the trunnion for pivotal movement in a clamp releasing direction and in an opposite clamping direction, the lever means being mounted for pivotal movement independent of the pivotal movement of the cam, the lever means being connected to a cam engaging means for engaging the cam and causing it to pivot with the lever when the lever is pivoted to a clamp releasing direction and for releasing the cam and permitting it to return to a clamping position as the lever is pivoted in the clamping direction.

3. The accessory clamping device of claim 2 wherein the lever is in frictional engagement with a slding surface, a sleeve bearing means is mounted on the trunnion and has a flange portion which bears against the lever, the flange portion comprises means for increasing the friction between the lever and the sliding surface.

4. The accessory clamping device of claim 3 wherein the trunnion comprises adjustable means engaging the sleeve bearing for displacing the sleeve bearing toward the lever, displacing the lever toward the sliding surface and thus increasing the pressure between the lever and the sliding surface.

5. The accessory clamping device of claim 2 wherein one of the lever and the cam has a recess and the other has a projection connected thereto, the projection and recess comprising the cam engaging means.

6. The accessory clamping device of claim 5 wherein the recess is an arcuate recess having an axial center which is common with the axis of the cam and the lever, and the projection moves in an arcuate path in the arcuate recess during operation of the lever.

7. The accessory clamping device of claim 6 wherein the recess includes an engaging surface means for engaging the projection when the lever is pivoted in a clamp releasing direction, whereby when the lever is pivoted, the projection engages the engaging surface means, causing the cam to rotate with the lever.

8. The accessory clamping device of claim 7 wherein the cam has a spiral clamping surrace, the distance between the stationary clamping surface and the opposing clamping surface of the cam increasing when the cam is rotated in the clamp releasing direction.

9. The accessory clamping device of claim 7 wherein the cam has a surface facing the lever, the arcuate recess is in said surface, and a projection connected to the lever extends into the arcuate recess.

10. The accessory clamping device of claim 2 wherein the trunnion extends from a housing element, the lever is mounted on the trunnion adjacent the housing element, a friction element is positioned between the lever and the housing element, the lever bearing against the friction element, a sleeve bearing is mounted on the trunnion having one end bearing against the surface of the lever opposite the friction element and the other end connected to an adjustment means for increasing the pressure of the sleeve bearing against the lever, thus increasing the friction between the lever and the friction element.

11. The accessory clamping device of claim 10 wherein the friction element is an integral surface of the housing.

12. The accessory clamping device of claim 10 wherein the friction element is a washer means positioned between the lever and the housing.

13. The accessory clamping device of claim 10 wherein the sleeve bearing supportingly engages the cam.

14. The accessory clamping device of claim 10 wherein the sleeve bearing extends through the axial center of the cam, and the spring means is a spiral torsion spring mounted in the cam concentric with the trunnion.

15. The accessory clamping device of claim 2 wherein the cam comprises first and second spiral cam surfaces which comprise clamping surfaces, a first cam surface being generated by a line parallel to the axis of rotation of the cam and the second surface being generated by a line forming an angle with the axis of rotation of the cam, the two cam surfaces intersecting.

16. The accessory clamping device of claim 15 wherein the second cam surface is generated by a line forming an angle of about 25° to 65° with the axis of rotation of the cam.

17. The accessory clamping device of claim 15 wherein the stationary clamping means includes first and second stationary clamping surfaces, the first stationary clamping surface being positioned opposite the first cam surface and the second stationary clamping surface being opposed to the second cam urface, first and second cam surfaces being configured to simultaneously decrease the distance between the first cam surface and the first stationary clamping surface and the distance between the second cam surface and the second stationary clamping surface when the cam is rotated in a support engaging direction.

18. The accessory clamping device of claim 2 wherein the stationary clamping surface is attached to the housing of a means for delivering parenteral solutions to a patient.

19. The accessory clamping device of claim 18 wherein the housing forms an element of the accessory clamping device.

* * * * *